United States Patent [19]

Helmlinger et al.

[11] 4,162,266
[45] Jul. 24, 1979

[54] TRIMETHYL-ACETYL OCTALINS, PROCESS FOR MAKING AND FRAGRANCE COMPOSITIONS CONTAINING SAME

[75] Inventors: Daniel Helmlinger, Dübendorf; Peter Naegeli, Wettingen, both of Switzerland

[73] Assignee: Givaudan Corporation, Clifton, N.J.

[21] Appl. No.: 695,349

[22] Filed: Jun. 14, 1976

[30] Foreign Application Priority Data

Jun. 25, 1975 [CH] Switzerland .................. 8251/75

[51] Int. Cl.² .......................................... C07C 49/61
[52] U.S. Cl. ...................... 260/586 F; 252/522; 260/586 C
[58] Field of Search .................. 260/586 C, 586 F

[56] References Cited

U.S. PATENT DOCUMENTS

| | | | |
|---|---|---|---|
| 2,222,357 | 11/1940 | Wolfe | 260/586 C |
| 2,230,005 | 1/1941 | Moser | 260/586 C |
| 2,933,506 | 4/1960 | Ohloff | 260/586 C |
| 3,076,022 | 1/1963 | Kitchens | 260/586 F |
| 3,852,358 | 12/1974 | Hall et al. | 260/586 C |
| 3,911,018 | 10/1975 | Hall et al. | 260/586 C |

*Primary Examiner*—Norman Morganstern
*Attorney, Agent, or Firm*—Thomas Cifelli, Jr.; Robert F. Tavares

[57] ABSTRACT

Novel trimethyl-acetyl-octalins mixtures are prepared by a Diels-Alder-type reaction involving methyl vinyl ketone and compounds having the structure

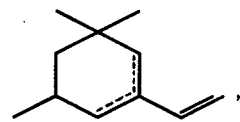
(II)

wherein one of the two lines denoted by dots represents an additional bond.

The novel compounds possess unique and unexpected desirable olfactory properties.

2 Claims, No Drawings

TRIMETHYL-ACETYL OCTALINS, PROCESS FOR MAKING AND FRAGRANCE COMPOSITIONS CONTAINING SAME

FIELD OF THE INVENTION

This invention relates to the field of fragrances and more especially to those involving novel mixtures of trimethyl-acetyl-octalins and a process for preparing the latter.

SUMMARY OF THE INVENTION

The fragrant mixtures provided by the present invention are mixtures of compounds of the general formula

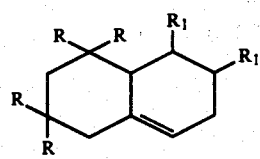

(I)

wherein three of the R-symbols represent methyl groups and the fourth R-symbol represents a hydrogen atom and one of the $R_1$-symbols represents a hydrogen atom and the other $R_1$-symbol represents an acetyl group.

Formula I includes the compounds hereinafter referred to as formulae Ia, Ib, Ic and Id.

According to the process provided by the invention, the fragrant mixtures aforesaid are manufactured by reacting a mixture of compounds of the formula

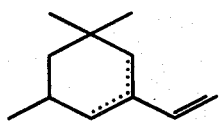

(II)

, wherein one of the two lines denoted by dots represents an additional bond, with methyl vinyl ketone.

The odorant mixtures provided by the present invention possess particular odorant properties. They can accordingly be used in the perfume industry for the production, in particular, of perfumes. They can also be used for the production of perfumed products; for example, for the perfuming of soaps, solid and liquid detergents, aerosols and cosmetic products of all kinds such as toilet water, salves, face-milk, make-up, lipsticks, bath salts and oils.

DESCRIPTION OF THE PREFERRED EMBODIMENTS

Formula I above includes compounds which are designated as formulae Ia, Ib, Ic and Id:

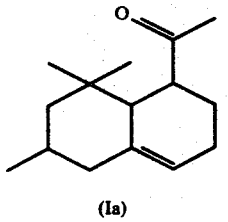

(Ia)

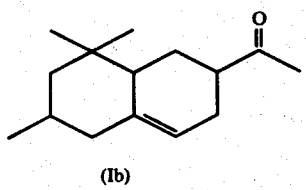

(Ib)

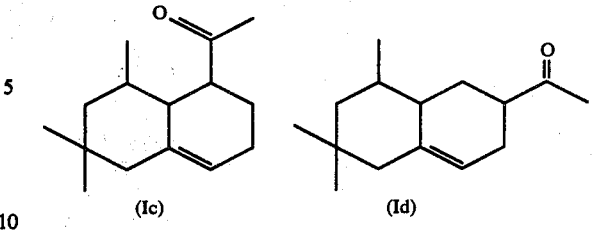

(Ic)    (Id)

According to the foregoing definition, the odorant mixtures provided by the present invention contain compounds of any of the four terminals Ia to Id. Because three asymmetric centres are present, the compounds of the four formulae Ia to Id can each occur in 8 enantiomeric forms or can each occur in the form of 4 enantiomer pairs.

According to the process provided by the invention, the odorant mixtures aforesaid are manufactured by reacting a mixture of compounds of the formula

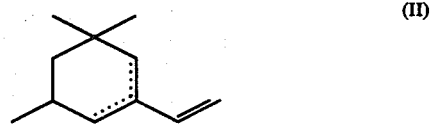

(II)

, wherein one of the two lines denoted by dots represents an additional bond, with methyl vinyl ketone.

The reaction of the mixture of compounds of formula II with methyl vinyl ketone can be carried out under the conditions of a Diels-Alder reaction according to methods known per se.

The reaction can be carried out in the presence or absence of an organic solvent such as, for example, an optionally-chlorinated aliphatic or aromatic hydrocarbon. Suitable solvents include hexane, benzene, toluene, carbon tetrachloride etc.

The suitable temperature range for the reaction is a temperature between about 120° C. and 250° C. In view of these elevated temperatures, the reaction is preferably carried out under pressure, unless there would then be used a high boiling solvent such as xylene etc.

The ratio of starting material of formula II to methyl vinyl ketone is not critical, but the methyl vinyl ketone is preferably used in a slight excess (e.g. a 10% excess).

The addition of an antioxidant (e.g. pyrogallol, hydroquinone monomethyl ether etc) to the reaction mixture is advantageous in order to prevent polymerisation of the reaction partner.

The isolation of the reaction product can be carried out, for example, by distillation of the reaction mixture.

The mixture of compounds of formula II can be obtained, for example, by dehydrating 3,3,5-trimethyl-1-vinyl-cyclohexanol, for example using p-toluenesulphonic acid or phosphorus oxychloride in pyridine etc. The mixture of compounds of formula II can also be obtained as a primary product in the reaction of 3,3,5-trimethyl-1-vinyl-cyclohexanol with citraconic acid anhydride (see Belgian Patent Specification No. 743,948, Example 6) or, in particularly high yield, by the thermal treatment of 3,3,5-trimethyl-1-vinyl-cyclohexanol in the gas phase over aluminium oxide.

The odorant mixtures provided by the present invention possess particular odorant properties. They can accordingly be used in the perfume industry for the production, in particular, of perfumes. They can also be used for the production of perfumed products; for example, for the perfuming of soaps, solid and liquid detergents, aerosols and cosmetic products of all kinds such as toilet water, salves, face-milk, make-up, lipsticks, bath salts and oils. In perfumes or in the perfumed products, the content of the odorant mixture can lie within wide limits; for example between about 10% in the case of detergents and about 20% in the case of alcoholic solutions. It will be appreciated that the content of odorant mixture can lie at above 20% in perfume bases or concentrates.

The odorant mixtures provided by the present invention provide a pronounced, warm, tobacco-like and amber-like fragrance of very good tenacity. They can be incorporated, for example, into odorant compositions of the tobacco, Chypre, lavender, amber, woody (especially spicy, root-like), modern men's line type. Such compositions are thereby modified in an advantageous manner in that they act fuller, softer, rounder and with more harmony.

The high stability of the odorant mixtures provided by the present invention and their pronounced tenacity enables them to be used as components of the most diverse compositions, especially since they are inexpensive (readily available starting material being used in the process and the reaction proceeding in high yields).

It will be appreciated from the foregoing that the invention also includes within its scope (a) an odorant composition which contains as an essential odour-imparting ingredient a mixture of compounds of formula I and (b) a method of imparting an odour to materials, which method comprises applying to said materials or incorporating therein an odour-imparting amount of a mixture of compounds of formula I or of an odorant composition as hereinbefore defined.

The following Examples illustrate the process provided by the present invention:

EXAMPLE 1

(a) A Grignard compound is prepared from 80 g of vinyl bromide and 20 g of magnesium in 1 litre of tetrahydrofuran. To this Grignard compound there are added dropwise at room temperature 100 g of 3,3,5-trimethylcyclohexanone (dihydroisophorone) in 100 ml of tetrahydrofuran. The mixture is held at reflux temperature for 12 hours. The mixture is then cooled, treated with saturated ammonium chloride solution and extracted with ether. The organic phase is washed neutral with saturated sodium chloride solution, dried and evaporated. The crude product is distilled in a high vacuum (55° C./0.1 mm Hg). There are obtained 88.9 g of 1-vinyl-1-hydroxy-3,3,5-trimethyl-cyclohexane.

(b) A mixture of 75 g of 1-vinyl-1hydroxy-3,3,5-trimethylcyclohexane and 2.3 g of p-toluenesulphonic acid in 350 ml of benzene is held at reflux temperature for 2 hours under a water separator. The mixture is cooled, washed neutral with water, dried and evaporated. The crude product is distilled in a high vacuum (73° C./10 mm Hg). There are thus obtained 28 g of 1-vinyl-3,3,5-(and 3,5,5-)trimethyl-cyclohex-1-ene.

(c) 34 g of 1-vinyl-3,3,5-(and 3,5,5-)trimethyl-cyclohex-1-ene and 17 g of methyl vinyl ketone are held at 180° C. for 12 hours under an argon atmosphere in an autoclave while adding a few crystals of hydroquinone monomethyl ether and pyrogallol. After cooling, the product is distilled and there are thus obtained 19.3 g of 1,1,3-(and 1,3,3-)trimethyl-7-(and 8)-acetyl-$\Delta^{5,10}$-octalin of boiling point 75°-100° C./0.2 mm Hg; IR (liq) 17.5 cm$^{-1}$; NMR (CDCl$_3$) 0.75 to 1.05 ppm, 9H, multiplet C—CH$_3$, C(CH$_3$)$_2$; 2.16 ppm, 3H, multiplet CO—CH$_3$; 5.6 ppm, 1H, multiplet C=CH; MS: M+ 220, 177, 161, 150, 135, 121. The fragrance of the product is warm, amber-like, tobacco-like, cedar-dry, earthy and spicy.

EXAMPLE 2

(a) 540 g of 1-vinyl-1-hydroxy-3,3,5-trimethyl-cyclohexane are slowly added dropwise (25 ml per hour) to a pyrolysis apparatus in a nitrogen stream on to heated (350° C.) aluminium oxide spheres (1.6 kg; particle size 3–5 mm) and the outflow is collected in a cooled cooling trap. The product is diluted with pentane, separated from the water and dried over sodium sulphate. The mixture is fractionally distilled over a Vigreux column. There are obtained 320 g of 1-vinyl-3,3,5-(and 3,5,5)-trimethyl-cyclohex-1-ene of boiling point 58°-61° C./10 mm Hg and 84 g of starting material (1-vinyl-1-hydroxy-3,3,5-trimethyl-cyclohexane of boiling point 79° C./10 mm Hg.

(b) If, in paragraph (a), the pyrolysis apparatus is provided with a pre-evaporator (180° C.), the conversion of the reaction partner is quantitative.

The following Example illustrates a typical odorant composition containing the odorant mixtures provided by this invention:

EXAMPLE A

Composition of the Chypre type:

|  | Parts by weight |
|---|---|
| 1,1,3-(and 1,3,3-)Trimethyl-7-(and 8)-acetyl-$\Delta^{5,10}$-octalin (compounds of formula I) | 70 |
| γ-Methylionone | 200 |
| Ambrette musk | 100 |
| Hydroxycitronellol | 80 |
| Bergamotte oil | 80 |
| Phenethyl alcohol | 70 |
| Lilial (p-tertbutyl-α-methyl)-hydrocinnamaldehyde) | 70 |
| α-Hexylcinnamaldehyde | 60 |
| Citronellol extra | 50 |
| Wood moss absolue | 50 |
| Vetiveryl acetate Bourbon | 50 |
| Patchouli oil | 40 |
| Eugenol extra | 40 |
| Gardenol | 20 |
| Citral-Base | 10 |
| Artemisia oil | 10 |
|  | 1000 |

Because of the presence of the odorant mixture of formula I, the composition acts full, round and with harmony.

What is claimed is:

1. An amber aroma-possessing mixture of compounds of the general formula

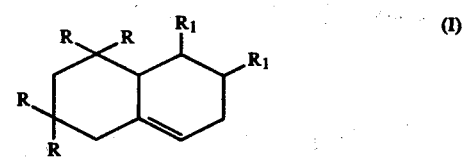

wherein three of the R-symbols represent methyl groups and the fourth R-symbol represents a hydrogen atom and one of the R$_1$-symbols represents a hydrogen atom and the other $R_1$-symbol represents an acetyl group.

2. An amber aroma-possessing mixture of 1,1,3-(and 1,3,3-)trimethyl-7-(and 8)-acetyl-$\Delta^{5,10}$-octalin having a boiling point of 75°–100° C./0.2 mm Hg; IR (liq.) 17.5 cm$^{-1}$; NMR (CDCl$_3$) 0.75 to 1.05 ppm, 9H, multiplet C-CH$_3$, C(CH$_3$)$_2$; 2.16 ppm, 3H, multiplet CO—CH$_3$; 5.6 ppm, 1H, multiplet C=CH; MS: M+ 220, 177, 161, 150, 135, 121.

* * * * *